US006488500B2

United States Patent
Rosenstatter

(10) Patent No.: US 6,488,500 B2
(45) Date of Patent: Dec. 3, 2002

(54) DENTAL HANDPIECE

(76) Inventor: Otto Rosenstatter, Matzing 16, A-5164 Seeham (AT)

(*) Notice: Subject to any disclaimer, the term of this patent is extended or adjusted under 35 U.S.C. 154(b) by 0 days.

(21) Appl. No.: 09/955,957

(22) Filed: Sep. 20, 2001

(65) Prior Publication Data
US 2002/0039716 A1 Apr. 4, 2002

(30) Foreign Application Priority Data
Sep. 22, 2000 (AT) .............................. 698/00 U

(51) Int. Cl.[7] ................................ A61C 1/07
(52) U.S. Cl. ......................... 433/120; 433/118
(58) Field of Search ..................... 433/118, 120, 433/124, 151

(56) References Cited

U.S. PATENT DOCUMENTS 2,960,314 A * 11/1960 Bodine, Jr. ............ 433/118
4,427,384 A * 1/1984 Sertich .................. 433/120
4,453,919 A * 6/1984 Takeshita ............... 433/120
4,484,892 A * 11/1984 Pernot et al. ........... 433/118
4,527,977 A * 7/1985 Nash ..................... 433/120
4,589,847 A * 5/1986 Loge et al. ............. 433/118
6,030,216 A   2/2000 Rosenstatter ........... 433/120

FOREIGN PATENT DOCUMENTS

AT          404550       12/1998

* cited by examiner

Primary Examiner—Cary E. O'Connor
(74) Attorney, Agent, or Firm—Wenderoth, Lind & Ponack, L.L.P.

(57) ABSTRACT

In a dental handpiece with an elastically arranged reception part (8) for a tool, compressed air from angled exit nozzles (9) can be applied to a sleeve (7) allocated to the reception part (8) with radial play. The circulating movement of the sleeve (7) is converted into a vibration of the reception part (8). The plane of vibration lies essentially perpendicular to the longitudinal axis of the reception part (8).

9 Claims, 2 Drawing Sheets

DENTAL HANDPIECE

BACKGROUND OF THE INVENTION

The invention relates to a dental handpiece with a workhead, in which rotation of an element to which compressed air can be applied is converted into vibration of an elastically housed reception part for a dental tool. The plane of vibration of the reception part lies essentially perpendicular to the longitudinal axis of the reception part.

Such a handpiece is known from FIG. 6 of AT 404 550 B. Incoming compressed air acts on an unbalanced turbine rotor which is housed rotatably on the reception part of the tool so that rotating unbalance generates the desired vibrations of the tool (file, brush, polishing tool, etc). Rotary shafts achieve up to 300,000 revolutions per minute and very high stresses inevitably occur in the roller bearings thereof.

SUMMARY OF THE INVENTION

The object of the invention is to create a dental handpiece of the type mentioned above, in which no roller bearings are necessary.

This is achieved according to the invention by having a vibration-generating element be formed by a sleeve allocated to the reception part with radial play, towards which sleeve angled outlet nozzles for compressed air are directed. The compressed air which strikes the wall of the sleeve at an angle effects a circular rolling movement of the sleeve, and thus generates the rotating unbalance which brings the reception part and the tool clamped in the reception part to natural oscillations.

In a first version, the angled outlet nozzles are provided inside the sleeve in the reception part. The compressed air is supplied to the outlet nozzles from an axially-distanced inlet chamber via an annular channel extending axially in the reception part, or via several axis-parallel channels.

In a further version, the angled outlet nozzles are provided outside the sleeve in an annular element connected to the reception part which surrounds the sleeve with radial play. As the annular element is connected to the reception part, the radial play between the sleeve and the annular element can be smaller than the radial play between the sleeve and the reception part itself, so that the sleeve circles against the internal wall of the annular element and the vibrations are transferred to the reception part via the annular element. The compressed air is supplied in this version via an annular channel which runs between the annular element and an external sleeve.

To act on the vibration-generating sleeve from the outside, the outlet nozzles can also, for example, be provided at an annular element arranged in the housing of the workhead.

For an elastic bearing of the reception part, a first elastic element in the front area of the reception part and a second elastic element in the rear area are preferably provided. The second elastic element preferably seals off the inlet chamber for the compressed air from the exit chamber. The sleeve is preferably arranged behind the second elastic element at the end of the reception part.

The invention is described in more detail in the following by means of the figures of the accompanying drawings without being limited to them.

DESCRIPTION OF THE PREFERRED EMBODIMENTS

Figure 1:
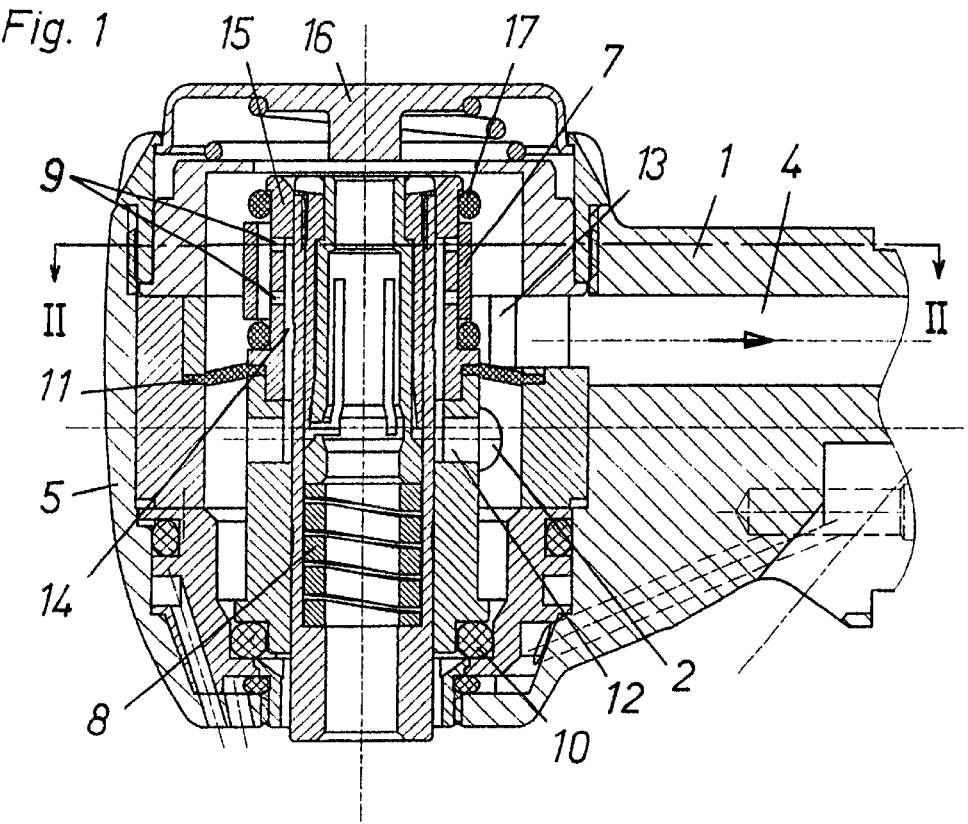
FIG. 1 is a sectional view along line I—I of FIG. 2 through a workhead of a handpiece of a first version.

A handpiece has a workhead 1, allocated to a grip area not shown, in which a channel 2 for the supply of compressed air and a channel 4 for return air are provided. In the housing 5 of the workhead 1, a reception part 8 for a dental tool is provided which contains a conventional clamping jaw which can be activated by a pushbutton 16 arranged on the rear side of the housing 5 at the top as shown in FIG. 1. The reception part 8 is arranged in a front elastic element 10 which is formed by an O-ring, and in a disk-shaped rear elastic element 11 in the housing 5. At the same time, the rear elastic element 11 seals off an inlet chamber 12, for the compressed air entering via channel 2, from an exit chamber 13 which communicates with the channel 4 for the return air. From the inlet chamber 12, which is provided approximately centrally in the housing 5, an annular channel 14 extends rearwardly into the area of a sleeve 7 which is allocated to the reception part 8 with radial play.

Figure 2:
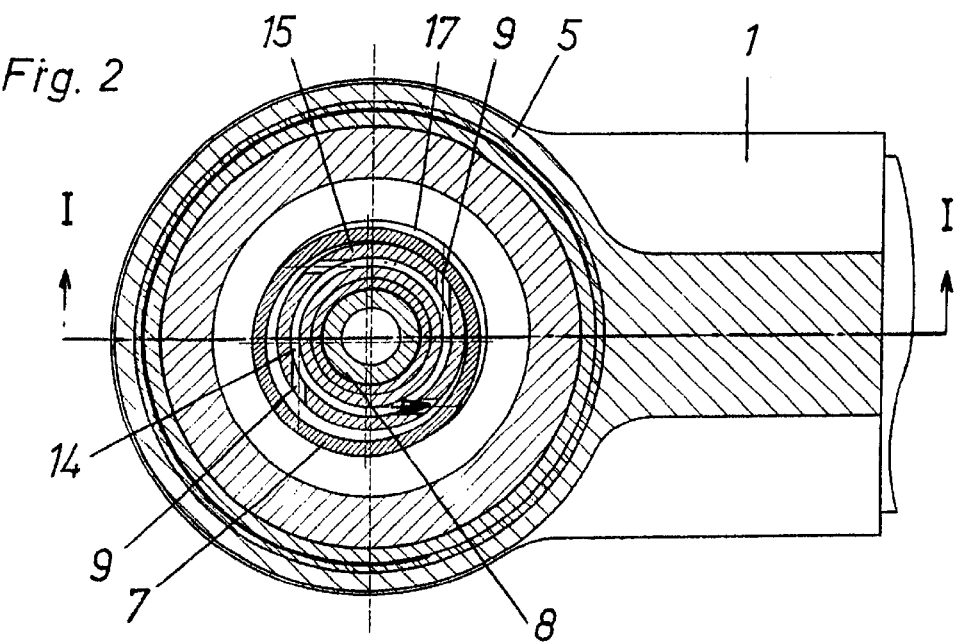
FIG. 2 is a sectional view along line II—II of FIG. 1.

In the version according to FIGS. 1 and 2, the sleeve 7 surrounds with radial play an annular element 15 fixed onto the reception part 8, which annular element 15 has annuli of angled outlet nozzles 9 in two planes, which lead almost tangentially from the annular channel 14 ending inside the annular element 15 through the wall of the annular element 15 to the outside. Emerging compressed air thus strikes at an angle the internal wall of the sleeve 7 which, because of the play, is set in a circulating movement about the reception part 8 or the annular element 15. The circulating movement generates the rotating unbalance which causes the reception part 8 to vibrate. The sleeve 7 is fixed in an axial direction by two O-rings 17. The space between the annular element 15 provided with the nozzles 9 and the sleeve 7 opens into the exit chamber 13 surrounding the sleeve 7, so that the air can escape into the channel 4.

Figure 3:
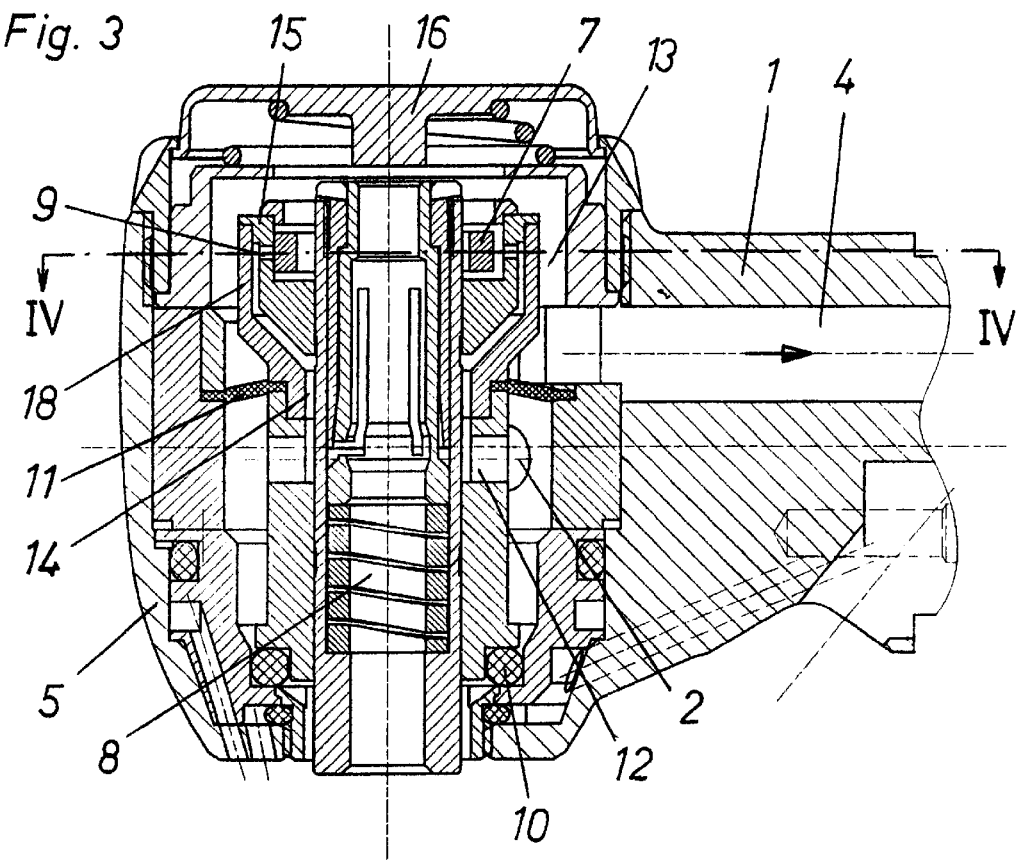
FIG. 3 is a sectional view along line III—III of FIG. 4 through a workhead of a handpiece of a second version.
Figure 4:
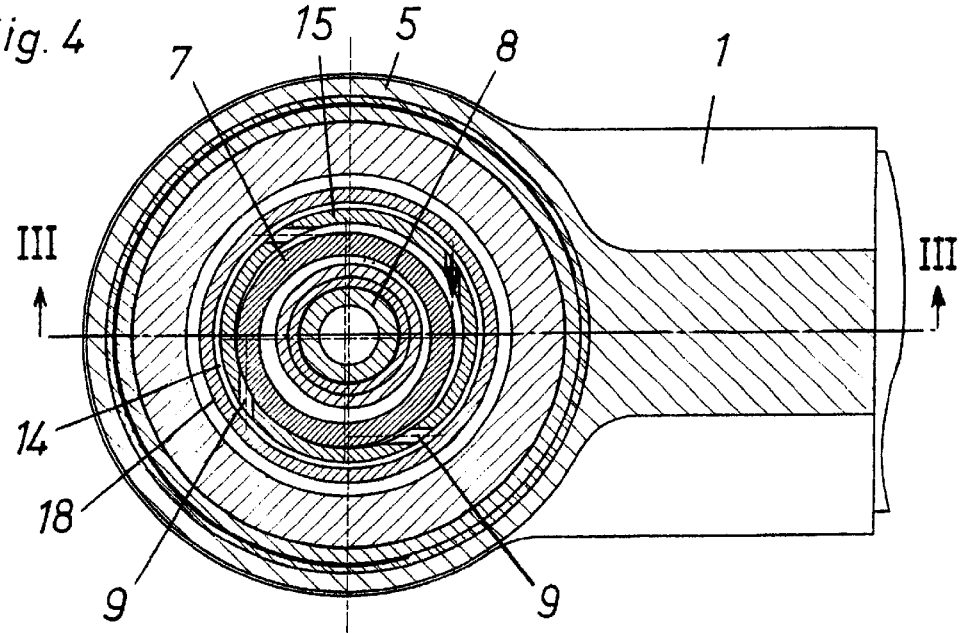
FIG. 4 is a sectional view along line IV—IV of FIG. 3.

In the version according to FIGS. 3 and 4, the annular element 15 connected to the reception part 8 has an approximately pot-shaped structure, and a housing chamber opening into the exit chamber 13 is provided between the reception part 8 and the annular element 15 for the loosely inserted sleeve 7. The angled outlet nozzles 9 in the wall of the annular element 15 are thus developed outside the sleeve 7, and the external and internal diameters are chosen so that the sleeve 7 circles against the inside of the annular element 15, while, as can be seen from FIGS. 3 and 4, a minimal gap remains relative to the reception part 8. To supply the compressed air, the annular channel 14 widens conically and ends outside the outlet nozzles 9, with the external limit of the annular channel 14 being formed by an additional external sleeve 18.

What is claimed is:

1. A dental handpiece with a workhead, said dental handpiece comprising:

a reception part that is elastically-housed;

a sleeve allocated to said reception part with radial play between said sleeve and said reception part; and angled outlet nozzles directed towards said sleeve, such that when compressed air is conveyed through said angled outlet nozzles against said sleeve said sleeve is caused to rotate which results in vibration of said reception part, with a plane of vibration of said reception part extending essentially perpendicular to a longitudinal axis of said reception part.

2. The dental handpiece according to claim 1, wherein said angled outlet nozzles are in said reception part and positioned within said sleeve.

3. The dental handpiece according to claim 2, further comprising:

an inlet chamber for compressed air;

an exit chamber; and an elastic bearing in a housing of the workhead, with said reception part being elastically-housed via said elastic bearing, wherein said elastic bearing includes a first elastic element for bearing against a front area of said reception part, and a second elastic element for bearing against a rear area of said reception part and sealing said inlet chamber from said exit chamber.

4. The dental handpiece according to claim 3, wherein said sleeve is behind said second elastic element.

5. The dental handpiece according to claim 1, further comprising:

an annular element connected to said reception part, wherein said angled outlet nozzles are in said annular element and positioned outside said sleeve.

6. The dental handpiece according to claim 5, further comprising:

an inlet chamber for compressed air;

an exit chamber; and an elastic bearing in a housing of the workhead, with said reception part being elastically-housed via said elastic bearing, wherein said elastic bearing includes a first elastic element for bearing against a front area of said reception part, and a second elastic element for bearing against a rear area of said reception part and sealing said inlet chamber from said exit chamber.

7. The dental handpiece according to claim 6, wherein said sleeve is behind said second elastic element.

8. The dental handpiece according to claim 1, further comprising:

an inlet chamber for compressed air;

an exit chamber; and an elastic bearing in a housing of the workhead, with said reception part being elastically-housed via said elastic bearing, wherein said elastic bearing includes a first elastic element for bearing against a front area of said reception part, and a second elastic element for bearing against a rear area of said reception part and sealing said inlet chamber from said exit chamber.

9. The dental handpiece according to claim 8, wherein said sleeve is behind said second elastic element.

* * * * *